United States Patent
D'Eredità

(10) Patent No.: US 7,163,557 B2
(45) Date of Patent: Jan. 16, 2007

(54) BIODEGRADABLE AURICULAR PROSTHETIC DEVICE

(76) Inventor: Riccardo D'Eredità, Via del Risorgimento, 30 I-35137, Padova (IT)

( * ) Notice: Subject to any disclaimer, the term of this patent is extended or adjusted under 35 U.S.C. 154(b) by 239 days.

(21) Appl. No.: 10/501,641

(22) PCT Filed: Jan. 16, 2002

(86) PCT No.: PCT/IT02/00792

§ 371 (c)(1),
(2), (4) Date: Jul. 15, 2004

(87) PCT Pub. No.: WO03/059406

PCT Pub. Date: Jul. 24, 2003

(65) Prior Publication Data

US 2005/0075733 A1    Apr. 7, 2005

(30) Foreign Application Priority Data

Jan. 16, 2002    (IT)    ............ PD2002A0005

(51) Int. Cl.
*A61F 2/18*    (2006.01)
*A61B 17/08*    (2006.01)

(52) U.S. Cl. .............. 623/10; 623/23.75; 606/151
(58) Field of Classification Search ............ 623/1.38, 623/10, 11.11, 16.11, 23.64, 23.75; 606/151
See application file for complete search history.

(56) References Cited

U.S. PATENT DOCUMENTS

| | | | | |
|---|---|---|---|---|
| 2,127,903 A | * | 8/1938 | Bowen | 606/154 |
| 3,620,218 A | * | 11/1971 | Schmitt et al | 606/154 |
| 4,650,488 A | * | 3/1987 | Bays et al. | 623/23.64 |
| 6,060,582 A | * | 5/2000 | Hubbell et al. | 528/354 |
| 6,077,916 A | * | 6/2000 | Laurencin et al. | 525/419 |
| 6,228,111 B1 | * | 5/2001 | Tormala et al. | 623/1.38 |
| 6,365,149 B1 | * | 4/2002 | Vyakarnam et al. | 424/93.1 |

* cited by examiner

*Primary Examiner*—David J. Isabella
(74) *Attorney, Agent, or Firm*—David A. Guerra

(57) ABSTRACT

A biodegradable auricular prosthetic device is described, particularly but not exclusively devised for the treatment of otitis media, comprising a tubular body having axially opposed ends and flanged at least at one of the opposed ends and at least a portion of which is produced from a material subject to biological degradation in the presence of organic liquids, wherein at least the portion made of material subject to biological degradation is produced from a polymeric material selected from the group of polyphosphazenes.

12 Claims, 1 Drawing Sheet

BIODEGRADABLE AURICULAR PROSTHETIC DEVICE

TECHNICAL FIELD

The subject of the present invention is a biodegradable auricular prosthetic device, particularly but not exclusively devised for the treatment of otitis media.

TECHNOLOGICAL BACKGROUND

The treatment of otitis media provides for a tubular ventilation device to be surgically implanted in the tympanic membrane to balance a pressure difference established between the middle ear and the outer ear. At one time such implants had to be surgically removed at the end of the treatment. Nowadays there have been devised, but hitherto never produced on an industrial scale, devices produced from biodegradable materials, such as polylactides, subject to biological degradation in the presence of organic liquids. An example of such devices (otherwise known as reabsorbable auricular ventilation tubes) is described in U.S. Pat. No. 4,650,488. The device described therein has a tapered body, of substantially frustoconical configuration, traversed axially by a hole and having a flanged end at the minor base. The device, or at least the flanged portion thereof, is produced from a biodegradable material based on polymers of lactic acid. Such a device has not hitherto been applied in the field inasmuch as it is potentially susceptible to exposing the patients in which it is implanted to numerous risks. Firstly, the polylactides involve the risk of growth of granulation tissues consequent upon their imperfect absorption by the tissues. The formation of granulation tissues is particularly risky in auricular treatments.

Moreover, both through the typical degradation of the material used and through the frustoconical configuration of the tapered body it involves the risk that the epithelial growth with which the hole for application of the prosthesis tends to close itself up again develops with invagination of the keratinized squamous epithelium, of the actual outer ear, along the conical portion and towards the middle ear, where mucous epithelium is present. There is in practice a risk of migration of the keratinized squamous epithelium towards the middle ear which is a possible cause of cholesteatoma.

All the problems in question have hitherto led to delays in the marketing of devices of the aforesaid type. Moreover, up to now there have not been reabsorbable auricular ventilation tubes approved by the FDA (Federal Drug Administration) of the United States.

DESCRIPTION OF THE INVENTION

The problem underlying the present invention is therefore that of making available a prosthetic device structurally and functionally designed to remedy all the drawbacks mentioned with reference to the prior art cited.

This problem is confronted and solved by the invention by means of a prosthetic device, such as an auricular ventilation tube, produced in accordance with the following claims.

BRIEF DESCRIPTION OF THE DRAWINGS

The characteristics and advantages of the invention will become clear from the description of a preferred exemplary embodiment thereof illustrated, by way of non-limiting example, with reference to the appended drawings, in which.

PREFERRED EMBODIMENT OF THE INVENTION

Figure 1:
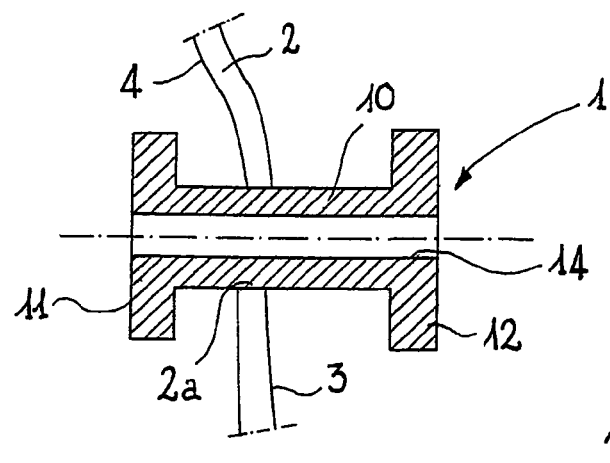
FIG. 1 is a view in longitudinal section of a prosthetic device according to the invention implanted in a tympanic membrane.
Figure 2:
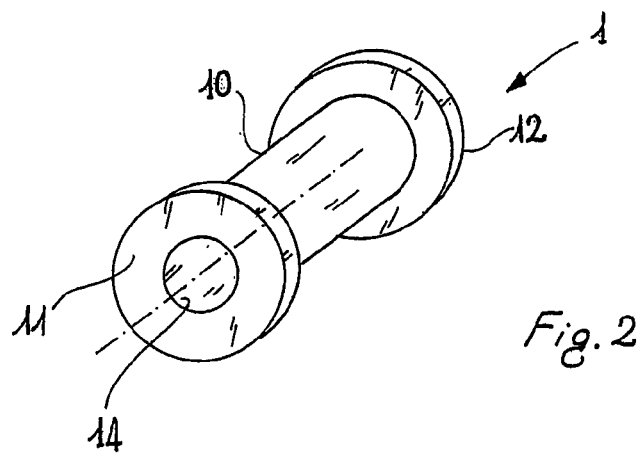
FIG. 2 is a perspective view of the device of FIG. 1.

In the drawings, the reference 1 indicates as a whole an auricular prosthetic device according to the invention, surgically implanted through a hole 2a made in the tympanic membrane 2 which sub-divides the ear into outer ear 3 and middle ear 4. The epithelial tissues of the outer ear 3 and middle ear 4 are respectively of the squamous type (cutis) and the mucous type. The device 1 comprises a tubular body having a cylindrical portion 10 of circular cross-section having two axially opposed ends with each of which there is associated, for example provided integrally, a respective flange 11, 12. The flange 11, in use as an implant, is located on the middle ear side with respect to the tympanic membrane, while the flange 12 is on the outer ear side. The tubular body is traversed by a through duct 14 which serves to ventilate the middle ear for the treatment of otitis (for example seromucosa).

At least the cylindrical portion 10 of the tubular body and the flange 11, but preferably the entire prosthetic device, is produced from a reabsorbable biodegradable material selected from the group of polyphosphazenes and relative polymeric compounds. The use of such materials and the relative formulation are described in U.S. Pat. No. 6,077,916, the content of which is considered as forming an integral part of the present description.

The production of the entire device (or of both the flanges) from biodegradable material renders it reversible, preventing the possibility of errors of orientation thereof in the implant site.

Preferably, the characteristics of biodegradability of the tubular body (understood as inclusive of the flanges) are variable along the axial extension thereof. For example, it has proved preferable for the speed of degradation of the cylindrical portion 10 to be greater than the speed of degradation of the flanges 11, 12. In this way the degradation of the cylindrical portion occurs with regular reduction of its cross-section and the occlusion of the implant hole occurs with regular regrowth of the tissues on both sides of the tympanic membrane, avoiding different mechanical stresses on the tissues, as well as the risk of invagination and consequent cholesteatoma. The variation of the degree of bioabsorption or biodegradability is obtained by means of irradiation (for example with gamma rays), since the areas subjected to greater irradiation generally assume a lesser molecular weight and an increase in the speed of degradation, or by producing the tubular body from different materials. Once the cylindrical portion 10 is severed, the inner flange 11 falls into the middle ear and is reabsorbed without giving rise to the growth of granulation tissue, while the outer flange 12 and the relative portion of cylindrical body fall into the outer ear and are expelled or reabsorbed without consequence. Moreover, the possibility is provided of incorporating into the structure of the polymer drugs, growth factors, bacteriostatic substances and/or bactericides.

Figures 3, 4, 5:
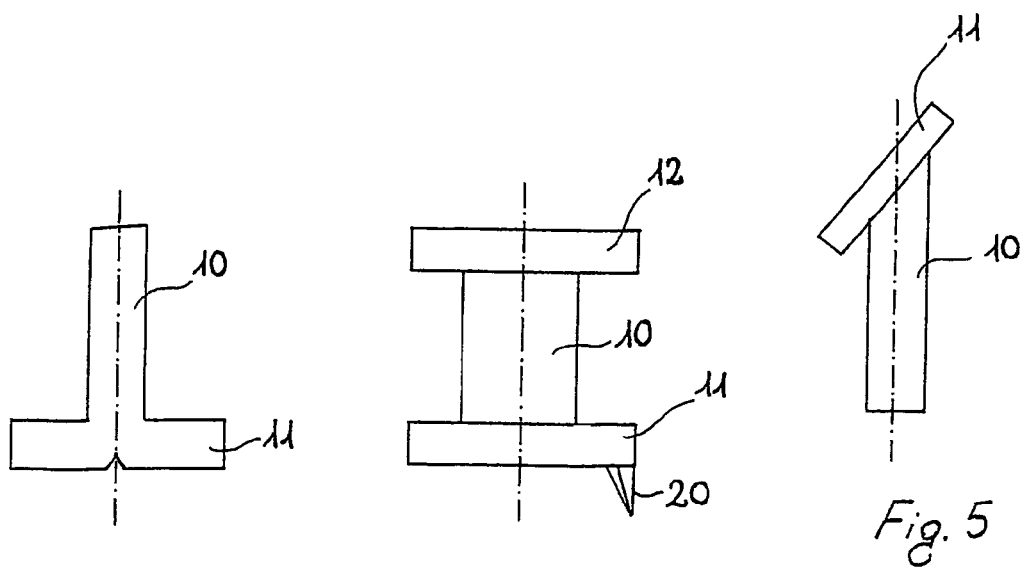
FIGS. 3 to 5 are views in elevation of the device of the present invention produced in three further configurations.

As has been emphasized, a first embodiment of the invention provides for the tubular body to be flanged at both the opposed ends in a bobbin configuration. Alternatively (FIG. 3) it is arranged for the flange 11 to be provided with a pointed appendage 20, for perforating the tympanic membrane at the implant site, or for the tubular body to be flanged at only one end (FIG. 4—in this case only the inner end 11) and further for said end flange to be oblique with respect to the axis of the cylindrical portion (FIG. 5). The oblique flange 11 serves in such a case as an "arrowhead" to facilitate the perforation of the tympanic membrane at the implant site.

The invention thus solves the problem posed, also providing numerous advantages, among which are:
- the possibility of establishing a priori, beforehand, the duration of permanence of the implant based on the therapeutic requirements;
- the abolition of the need for removal with a consequent second surgical procedure (and the need for anaesthesia in children);
- the reduction of the risk of residual permanent tympanic perforation;
- the possibility of incorporating into the structure of the polymer drugs, growth factors, bacteriostatic substances and/or bactericides.

The invention claimed is:

1. A biodegradable auricular prosthetic device, particularly but not exclusively devised for the treatment of otitis media, comprising a tubular body having axially opposed ends and flanged at least at one of said opposed ends and at least a portion of which is produced from a material subject to biological degradation in the presence of organic liquids, characterized in that at least said portion made of material subject to biological degradation is produced from a polymeric material selected from the group of polyphosphazenes; wherein said tubular body has a duct defined therethrough; wherein at least said portion made of material subject to biological degradation has variable biodegradability characteristics along the axial extension of said tubular body; and wherein said tubular body, in an intermediate portion thereof comprised between said ends, has a greater biodegradability with respect to the biodegradability of said flange.

2. The prosthetic device according to claim 1, wherein said body is flanged at both said opposed ends in a bobbin shape.

3. The prosthetic device according to claim 2, wherein there are incorporated into said polymeric material substances selected from the group consisting of drugs, growth factors, bacteriostatic substances, and bactericides.

4. The prosthetic device according to claim 3, wherein one of said flanges is made of a biodegradable polymeric material selected from the group of polyphosphazene, said biodegradable flange is located at said end of said tubular body having the greatest rate of biodegradability.

5. The prosthetic device according to claim 4, wherein the speed of degradation of said tubular body material is greater than the speed of degradation of said flange.

6. The prosthetic device according to claim 5, wherein said biodegradable flange further comprising a pointed appendage extending out therefrom, said appendage being adapted to perforate the tympanic membrane when inserted into an ear.

7. The prosthetic device according to claim 1, wherein said flange is oblique with respect to the axis of said tubular body, and said flange is located at said end of said tubular body having the lowest rate of biodegradability.

8. A biodegradable auricular prosthetic device for ventilating the middle ear of a patient, said prosthetic device comprising:
- a tubular body having axially opposed ends and a duct defined therethrough, said tubular body being made of material subject to biological degradation selected from the group of polyphosphazenes, wherein said tubular body has variable biodegradability characteristics along the axial extension of said tubular body;
- an inner flange attached to said end of said tubular body having the greatest rate of biodegradability, said inner flange being made of material subject to biological degradation selected from the group of polyphosphazenes; and
- an outer flange attached to said end opposite said inner flange;
- wherein there are incorporated into said polymeric material substances selected from the group consisting of drugs, growth factors, bacteriostatic substances, and bactericides;
- wherein the speed of degradation of said tubular body material is greater than the speed of degradation of said inner flange.

9. The prosthetic device according to claim 8, wherein said inner flange further comprising a pointed appendage extending out therefrom, said appendage being adapted to perforate the tympanic membrane when inserted into the ear.

10. The prosthetic device according to claim 9, wherein said outer flange being made of material subject to biological degradation selected from the group consisting of polyphosphazenes.

11. The prosthetic device according to claim 10, wherein the speed of degradation of said tubular body material is greater than the speed of degradation of said outer flange.

12. A biodegradable auricular prosthetic device comprising:
- a tubular body having axially opposed ends and a duct defined therethrough, said tubular body being made of material subject to biological degradation selected from the group of polyphosphazenes, wherein said tubular body has variable biodegradability characteristics along the axial extension of said tubular body;
- an inner flange attached to said end of said tubular body having the greatest rate of biodegradability, said inner flange being made of material subject to biological degradation selected from the group of polyphosphazenes;
- a pointed appendage extending out from said inner flange away from said tubular body, said appendage being made of material subject to biological degradation selected from the group of polyphosphazenes; and
- an outer flange attached to said end opposite said inner flange, said outer flange being made of material subject to biological degradation selected from the group of polyphosphazenes;
- wherein there are incorporated into said polymeric material substances selected from the group consisting of drugs, growth factors, bacteriostatic substances, and bactericides;
- wherein the speed of degradation of said tubular body material is greater than the speed of degradation of said inner and outer flanges.

* * * * *